United States Patent
Haga et al.

(10) Patent No.: US 11,642,306 B2
(45) Date of Patent: *May 9, 2023

(54) FERMENTED HONEY PRODUCT AND PRODUCTION METHOD THEREFOR

(71) Applicant: YAMADA BEE COMPANY, INC., Okayama (JP)

(72) Inventors: Asami Haga, Okayama (JP); Madoka Isoe, Okayama (JP); Ayanori Yamaki, Okayama (JP); Yuka Kimura, Okayama (JP)

(73) Assignee: YAMADA BEE COMPANY, INC., Okayama (JP)

( * ) Notice: Subject to any disclaimer, the term of this patent is extended or adjusted under 35 U.S.C. 154(b) by 384 days.

This patent is subject to a terminal disclaimer.

(21) Appl. No.: 16/474,055

(22) PCT Filed: Dec. 21, 2017

(86) PCT No.: PCT/JP2017/046025
§ 371 (c)(1),
(2) Date: Aug. 15, 2019

(87) PCT Pub. No.: WO2018/123827
PCT Pub. Date: Jul. 5, 2018

(65) Prior Publication Data
US 2020/0383901 A1    Dec. 10, 2020

(30) Foreign Application Priority Data

Dec. 28, 2016 (JP) ............................. JP2016-255749

(51) Int. Cl.
| | |
|---|---|
| *A61K 8/98* | (2006.01) |
| *A23L 21/25* | (2016.01) |
| *A23L 33/135* | (2016.01) |
| *A61K 8/99* | (2017.01) |
| *A61K 35/644* | (2015.01) |
| *A61K 35/747* | (2015.01) |
| *A61Q 19/00* | (2006.01) |

(52) U.S. Cl.
CPC .............. *A61K 8/988* (2013.01); *A23L 21/25* (2016.08); *A23L 33/135* (2016.08); *A61K 8/99* (2013.01); *A61K 35/644* (2013.01); *A61K 35/747* (2013.01); *A61Q 19/00* (2013.01)

(58) Field of Classification Search
CPC .................................. A61K 8/90; A23L 21/25
See application file for complete search history.

(56) References Cited

U.S. PATENT DOCUMENTS 10,933,101 B2 *    3/2021 Haga ................ A61Q 19/005
2014/0363880 A1    12/2014 Matsuura et al.

FOREIGN PATENT DOCUMENTS

| CN | 103789138 A | 5/2014 |
|---|---|---|
| EP | 3069616 A2 | 9/2016 |
| JP | 2010/263858 A | 11/2010 |
| JP | 2014-028781 A | 2/2014 |
| JP | 5536640 B2 | 7/2014 |
| JP | 2015/223106 A | 12/2015 |
| WO | WO 2013/099883 A1 | 7/2013 |
| WO | WO 2008/136730 A1 | 11/2018 |

OTHER PUBLICATIONS

Communication forwarding the extended European Search Report dated Jul. 27, 2020 for European Patent Application No. 17888145.4, 15 pages.
Database WPI, Week 201610; Thomson Scientific Nov. 25, 2015; XP002799757, 1 page.
International Search Report dated Mar. 20, 2018 for International Patent Application No. PCT/JP2017/046025, 2 pages.
International Preliminary Report on Patentability dated Jul. 2, 2019 for International Patent Application No. PCT/JP2017/046025, 8 pages.
Endo, et al: "Characterization and emended description of *Lactobacillus kunkeei* as a fructophilip lactic acid bacterium", International Journal of Systemic and Evolutionary Microbiology, Mar. 1, 2012, vol. 62, pp. 500-504.
Molan, Peter: "The antibacterial activity of honey: 1. The nature of the antibacterial activity", Bee World, 1992, vol. 73, No. 1, pp. 5-28.
Molan, Peter: "The potential of honey to promote oral wellness", General Dentistry, Nov.-Dec. 2001, vol. 49, No. 6, pp. 584-589.
Muramatsu, et al: "Growth of and fructooligosaccharide-hydrolying enzyme production in *Bifidobacterium* spp. cultured pm 5-30% honey", J. Rakuno Gakuen Univ, 2009, vol. 34, No. 1, pp. 1-5, Abstract.
Neveling, et al: "Fructophilic *Lactobacillus kunkeei* and *Lactobacillus brevis* isolated from fresh flowers, bees and bee-hives", Curr Microbiology, Jul. 15, 2012, vol. 65, pp. 507-515.
Yumihara, Kazuyo: "Regarding effects of honey on growth of lactobacillus", Lecture abstract of 63$^{rd}$ The Japanese Society for Food Science and Technology, Aug. 25, 2016, p. 141, 3Bp8, with English translation, 5 pages.

* cited by examiner

*Primary Examiner* — Gina C Justice
(74) *Attorney, Agent, or Firm* — Squire Patton Boggs (US) LLP (57) ABSTRACT

The present invention provides a fermented honey product obtained by fermenting a honey-containing material having a honey concentration of more than 25% with *Lactobacillus kunkeei*.

8 Claims, 5 Drawing Sheets

FERMENTED HONEY PRODUCT AND PRODUCTION METHOD THEREFOR

TECHNICAL FIELD

The present invention relates to a fermented honey product and a production method therefor.

BACKGROUND ART

Honey is a nutrient-rich material. Fermented honey products have been used as foods. For instance, Patent Literature 1 discloses a process for producing a health drink, comprising fermenting honey with lactic bacteria, etc. In Patent Literature 1, the concentration of honey used as a fermentation starting material is about 15% or less.

CITATION LIST

Patent Literature

[Patent Literature 1] CN103789138 A

Non Patent Literature

[Non Patent Literature 1] J. Rakuno Gakuen Univ., 34(1), 1-5, 2009.
[Non Patent Literature 2] Bee world, 73(1), 5-28, 1992.
[Non Patent Literature 3] General Dentistry, 49(6), 584-589, 2001.

SUMMARY OF INVENTION

Technical Problem

Sugars of honey can be a nutritional source for bacteria other than fermentative bacteria, so that unwanted microbes may grow during fermentation when the honey concentration is low. However, there is a problem to ferment a highly concentrated honey-containing material because no fermentative bacteria have been known that are viable in the highly concentrated honey-containing material due to the high osmotic pressure effects, etc. For instance, Non Patent Literature 1 shows that *Bifidobacterium* cells were cultured using honey as a carbon source; and when the concentration of honey in medium was 20% or more, growth of the bacterial cells was not observed. Non Patent Literature 2 describes that growth of *Streptococcus* is completely suppressed at a honey concentration of 25% or less. In addition, Non Patent Literature 3 describes that growth of *Lactobacillus casei* is suppressed at a honey concentration of from 8 to 12%.

The purpose of the present invention is to provide a fermented product obtained by fermenting a highly concentrated honey-containing material.

Solution to Problem

The present inventors have discovered that *Lactobacillus kunkeei* can be used to ferment a highly concentrated honey-containing material.

An aspect of the present invention provides a fermented honey product obtained by fermenting a honey-containing material with *Lactobacillus kunkeei*, wherein the material has a honey concentration of more than 25%.

The *Lactobacillus kunkeei* is preferably *Lactobacillus kunkeei* BPS402 (accession number: FERM BP-11439).

Another aspect of the present invention provides a food, cosmetic, drug, or quasi-drug comprising the fermented honey product. The fermented honey product contains an active ingredient such as lactic acid and/or acetic acid and is produced in a hygienic environment. Accordingly, this fermented honey product can be suitably used as a food, cosmetic, drug, or quasi-drug.

Still another aspect of the present invention provides a method for producing a fermented honey product, comprising a step of fermenting a honey-containing material having a honey concentration of more than 25% with *Lactobacillus kunkeei*.

The *Lactobacillus kunkeei* is preferably *Lactobacillus kunkeei* BPS402 (accession number: FERM BP-11439).

Still yet another aspect of the present invention provides a method for producing a food, cosmetic, drug, or quasi-drug, comprising a step of adding the fermented honey product obtained by the above production method.

A further aspect of the present invention provides a composition for fermentation of a honey-containing material having a honey concentration of more than 25%, the composition comprising *Lactobacillus kunkeei*. The composition for fermentation can be used to ferment a highly concentrated honey-containing material and may be used to produce a fermented honey product in an environment under which unwanted microbes hardly grow.

The *Lactobacillus kunkeei* is preferably *Lactobacillus kunkeei* BPS402 (accession number: FERM BP-11439).

The present invention can be said to be *Lactobacillus kunkeei* or a *Lactobacillus kunkeei*-containing composition for use in fermenting a honey-containing material having a honey concentration of more than 25%. The present invention can also be said to be an application using *Lactobacillus kunkeei* as a composition for fermenting a honey-containing material having a honey concentration of more than 25% or an application using *Lactobacillus kunkeei* for the production of a composition for fermenting a honey-containing material having a honey concentration of more than 25%.

Advantageous Effects of Invention

The present invention can provide a fermented honey product obtained by fermenting a highly concentrated honey-containing material.

DESCRIPTION OF EMBODIMENTS

Hereinafter, embodiments of the present invention will be described in detail. However, the present invention is not limited to the following embodiments. As used herein, unless otherwise indicated, the "%" means "mass %".

A fermented honey product according to an embodiment of the present invention is obtained by fermenting a honey-containing material having a honey concentration of more than 25% with *Lactobacillus kunkeei*.

Honey is produced by honeybees from syrup collected from plant nectar, sap, plant parasite secretions, etc. as a main source material. Examples of kinds of honey as a starting material to be fermented in this embodiment include, but are not particularly limited to, manuka honey, acacia honey, honeydew honey, clover honey, orange honey, milk vetch honey, rosemary honey, sunflower honey, rape blossom honey, and coffee honey. The honeys may be used singly or in combination of two or more. It is preferable that the honey is acacia honey. The kinds of honeybees used for honey collection and where the honey is originated are not particularly limited.

*Lactobacillus kunkeei* can ferment a highly concentrated honey-containing material, which other types of microorganism are not able to ferment. It is preferable that *Lactobacillus kunkeei* used for producing a fermented honey product according to this embodiment shows assimilating ability for glucose and fructose. It is also preferable that it shows assimilating ability for glucose, fructose, sucrose, trehalose, and gluconic acid salts.

The *Lactobacillus kunkeei* is preferably *Lactobacillus kunkeei* BPS402. *Lactobacillus kunkeei* BPS402 has been deposited as the accession number: FERM P-22177 on Oct. 3, 2011, in the Patent Microorganisms Depositary of the National Institute of Advanced Industrial Science and Technology (Chuo 6, 1-1-1 Higashi, Tsukuba-shi, Ibaraki Prefecture (Zip code: 305-8566), Japan) and is available. In addition, the bacterial strain has been transferred to the international depositary authority and its accession number is FERM BP-11439. Access to the biological deposit of *Lactobacillus kunkeei* is granted irrevocably for the term of the patent issuing from this application.

The above *Lactobacillus kunkeei* is useful as a starter for fermenting a highly concentrated honey-containing material. Thus, the present invention also provides a composition for fermentation of a honey-containing material having a high honey concentration, for instance, a honey concentration of more than 25%, the composition comprising the above *Lactobacillus kunkeei*. The composition for fermentation of a honey-containing material having a high honey concentration is a composition to be used for producing a fermented honey product by fermenting a highly concentrated honey-containing material, and may be used as a starter to be inoculated into the highly concentrated honey-containing material. The composition for fermentation may consist of *Lactobacillus kunkeei*.

An embodiment of the present invention provides *Lactobacillus kunkeei* or a *Lactobacillus kunkeei*-containing composition to be used for fermenting a honey-containing material having a honey concentration of more than 25%. Another embodiment of the present invention provides an application using *Lactobacillus kunkeei* as a composition for fermenting a honey-containing material having a honey concentration of more than 25%. Still another embodiment of the present invention provides an application using *Lactobacillus kunkeei* for the production of a composition for fermenting a honey-containing material having a honey concentration of more than 25%.

Culture of *Lactobacillus kunkeei* may be carried out in accordance with a conventional method. The culture medium is not particularly limited as long as the bacteria can be cultured, and examples include natural medium, synthetic medium, and semi-synthetic medium. The medium used may contain a nitrogen source and a carbon source. Examples of the nitrogen source include meat extracts, peptones, casein, yeast extracts, gluten, soybean powder, soybean hydrolysates, and amino acids. Examples of the carbon source include glucose, lactose, fructose, inositol, sorbitol, starch syrup, starch, malted rice extracts, bran, bagasse, and molasses. It is also possible to add inorganic matter (e g, ammonium sulfate, potassium phosphate, magnesium chloride, sodium chloride, calcium carbonate, iron, manganese, molybdenum) and/or various vitamins, etc.

The culture temperature may be, for instance, from 4 to 45° C., preferably from 25 to 40° C., and more preferably from 28 to 33° C. The culture period may be, for instance, from 8 to 72 hours. The culturing may be carried out by aeration shaking or aeration stirring. The pH of the culture medium may be, for instance, from 4.0 to 9.0 and preferably from 6.0 to 8.0. The culturing method includes, for example, inoculating a bacterial cell(s) in MRS medium and culturing them at 30° C. for 48 h.

The bacterial liquid obtained by culturing *Lactobacillus kunkeei* may be used, as it is, for fermentation by inoculating the liquid in a honey-containing material, or may be diluted with medium, etc., for usage. The fermentation of a honey-containing material by *Lactobacillus kunkeei* can be carried out at, for instance, 4 to 45° C. and preferably at 25 to 40° C. The fermentation duration may be, for instance, from 12 to 60 h and preferably from 24 to 48 h. The pH of a honey-containing material when the fermentation starts may be, for instance, from 3 to 8 and preferably from 4 to 6. The pH of a honey-containing material tends to decrease during fermentation as acids such as lactic acid and acetic acid are produced more. The fermentation may be carried out by aeration shaking or aeration stirring.

The honey concentration in the honey-containing material to be fermented is more than 25%. The honey content of the honey-containing material to be fermented may be more than 25% and less than 35%, preferably from 28 to 34%, and more preferably from 28 to 32%. In addition, the solid content of honey per total volume of a honey-containing material to be fermented may be, for instance, 20% or more, preferably for 20 to 28%, more preferably from 22.4 to 27.2%, and still more preferably from 22.4 to 25.6%.

The honey-containing material may be in a form allowing for fermentation by *Lactobacillus kunkeei* and examples of the form may include liquids, pastes and gels. For instance, a honey-containing material may be a product which honey is dissolved or suspended in water. The honey-containing material to be fermented may further contain, for example, a nitrogen source, a carbon source or the like. It is preferable that the honey-containing material to be used for fermentation is sterilized by heating, etc.

In the step of producing a fermented honey product according to this embodiment, a highly concentrated honey-containing material is fermented. Thus, due to the osmotic pressure and honey's antimicrobial effects, unwanted microbes hardly grow during the fermentation. In addition, the fermented product contains acetic acid, so that the resulting fermented product is highly antibacterial.

The fermented honey product according to this embodiment may be a product, as it is, produced by fermentation or may be processed by heating, filtration, concentration, evaporation to dryness, lyophilization, etc. The fermented honey product according to this embodiment may contain *Lactobacillus kunkeei* viable cells and/or dead cells, which may be separated and removed by filtration, etc. The fermented honey product may contain, for instance, organic acids such as lactic acid and acetic acid, vitamins, amino acids, minerals, trace elements, and/or polyphenol. The fermented honey product may contain alcohol but is preferably does not contain alcohol. Since the fermented honey product is obtained by fermenting honey, it can be expected that the content of vitamins, amino acids, and others are increased when compared to that of starting material honey and that organic acids, which are not contained in the starting material honey, is produced.

The fermented honey product according to this embodiment contains lactic acid and acetic acid. Lactic acid is one of major components in a natural moisturizing factor (NMF), which has been known as a skin moisture-retaining factor, and the fermented honey product according to this embodiment exerts beauty effects such as skin moisture retention. Meanwhile, because acetic acid is an antimicrobial substance, the fermented honey product according to this embodiment can exert antimicrobial effects. The concentration of lactic acid in the fermented honey product may be, for instance, from 500 to 3000 ppm. The concentration of acetic acid may be, for instance, from 500 to 2500 ppm.

The fermented honey product according to this embodiment is obtained by fermenting a highly concentrated honey-containing material with *Lactobacillus kunkeei*. This results in characteristics different from those of a fermented product obtained by fermenting a material containing a low concentration of honey. A honey-containing material to be fermented may be, for example, a honey-containing liquid. In this case, the resulting fermented honey product has a low water content percentage, which may be, for instance, from 65 to 90%, 65 to 80%, or 65 to 75%. The fermented honey product according to this embodiment is unlikely to be contaminated with other microbes because it is obtained by fermenting highly concentrated honey.

The above fermented honey product, by itself, can be used for a food, cosmetic, drug, or quasi-drug, or the product can be used as a component thereof. The above fermented honey product may be used as it is, or optionally be diluted, dried, and/or enriched, etc., to provide it in a form of a liquid, a solid, a paste, or the like, as a food, cosmetic, drug, or quasi-drug, or a component thereof.

The food according to an embodiment of the present invention contains the above fermented honey product. The food may be a beverage. The concentration of fermented honey product in the fermented honey product-containing food according to this embodiment may be, for instance, from 0.1 to 100%. The fermented honey product-containing food may be optionally combined with minerals, vitamins, flavonoids, quinones, polyphenols, amino acid, nucleic acid, essential fatty acid, a refrigerant, a binding agent, a sweetener, a disintegrator, a lubricant, a colorant, a flavor, a stabilizer, an antiseptic, a sustained release adjusting agent, a surfactant, a resolvent, and/or a wetting agent. The food may be in any form such as a solid, liquid, paste, etc.

Examples of the food include the following and the food can be produced by adding the above fermented honey product to an intermediate product or a final product in a manufacturing step therefor: beverages such as refreshers (e.g., juices, tee drinks), milk drinks, lactic bacteria-containing beverages, yogurt beverages, sodas, coffees, and alcohol drinks (e.g., sakes, Western liquors, wines, honey liquors); spreads (e.g., custard cream); pastes (e.g., fruit pastes); Western sweets (e.g., chocolates, donuts, pies, cream puffs, chewing gums, jellies, candies, cookies, cakes, puddings); Japanese sweets (e.g., "daifuku", rice cakes, sweet buns, Castella, "anmitsu", "yokan"); ices (e.g., ice creams, ice candies, sorbets); cooked foods (e.g., curries, "gyudon", rice porridges, miso-soups, soups, meat sources, pastas, pickles, jams); and seasonings (e.g., dressings, a rice seasoning, flavor enhancers, soup bases).

The food according to this embodiment may be a food having an enhanced tertiary function (body condition-controlling function). Examples of the food having an enhanced tertiary food function include health foods, foods with function claims, nutraceuticals, supplements, and foods for specified health uses.

The cosmetic according to an embodiment of the present invention contains the above fermented honey product as an active ingredient. The fermented honey product-containing cosmetics should exert beauty effects such as moisture retention. Additionally, because the above fermented honey product contains acetic acid, the above cosmetics should exert, without adding any preservative, antimicrobial effects. The cosmetic according to this embodiment is applicable to, for instance, the skin, mucosa, body hairs, head hairs, head skin, nails, teeth, face skin, lips of each animal including a human. The concentration of fermented honey product in the fermented honey product-containing cosmetic according to this embodiment may be, for instance, from 0.1 to 100%.

In addition to the fermented honey product, common cosmetic components such as a whitening agent, a moisturizing agent, an antioxidant, an oily component, a UV absorber, a surfactant, a thickener, alcohols, a powder component, a colorant, an aqueous component, water, and/or various nutrients for the skin can be optionally added to the cosmetic according to this embodiment. The cosmetic according to this embodiment may be produced by adding the above fermented honey product to an intermediate product or a final product of the producing steps of the cosmetic.

Examples of a dosage form of cosmetic according to this embodiment include solubilizer-based, emulsifier-based, powder-based, oil-based, gel-based, ointment-based, aerosol-based, water-oil bilayer-based, and water-oil-powder three-layer-based dosage forms. Examples of the above cosmetics may include basic cosmetics (e.g., a face wash, skin lotion, milky lotion, cream, gel, essence, serum, pack, mask, mist, UV protector); make-up cosmetics (e.g., a foundation cream, lip stick, cheek rouge, eyeshadow, eyeliner, mascara); and face washes, massage preparations, cleansing agents, after-shave lotions, pre-shave lotions, shaving creams, body soaps, soaps, shampoos, conditioners, hair treatment agents, hair preparations, hair tonics, hair mists, hair foams, hair liquids, hair gels, hair sprays, hair growth agents, antiperspirants, bath additives, mouth rinses, oral cosmetics, and toothpastes.

The drug or a quasi-drug according to an embodiment of the present invention contains the above fermented honey product as an active ingredient. The above drug and quasi-drug may be produced by a process including adding the above fermented honey product to other ingredients optionally used. The fermented honey product, as it is, may be used for a drug or quasi-drug. Examples of the dosage form that can be used include tablets (including uncoated tablets, sugar-coated tablets, effervescent tablets, film-coated tablets, chewable tablets, pastilles), capsules, pills, powders (powdered medicines), fine granules, granules, liquids, suspensions, emulsions, syrups, pastes, and injections (including cases where when used, distilled water or an infusion solution such as an amino acid infusion solution or an electrolyte infusion solution is mixed therewith to prepare a liquid injection). Each of the above preparations may be prepared by, for instance, mixing a fermented honey product, which is an active ingredient, optionally with another component(s) to produce each preparation in the above dosage forms.

The solid content of fermented honey product per total volume of the drug or quasi-drug according to this embodiment may be, for instance, from 0.1 to 100%. The drug or quasi-drug according to this embodiment may be used as, for example, an antimicrobial because of an antimicrobial component, such as acetic acid, in the fermented honey product included as an active ingredient.

EXAMPLES

Hereinafter, the present invention will be more specifically described based on Examples. However, the present invention is not limited to the following Examples.

The following five *Lactobacillus* bacterial strains were used. Table 1 shows the optimal culture conditions for each bacterium.

*Lactobacillus kunkeei* BPS402
*L. plantarum* NBRC14712
*L. brevis* NBRC12005
*L. delbrueckii* subsp. *Bulgaricus* NBRC13953
*L. casei* NBRC15883

TABLE 1

| Bacterium Name | BPS402 | | *L. plantarum* | | *L. brevis* | | *L. delbrueckii* | | *L. casei* | |
|---|---|---|---|---|---|---|---|---|---|---|
| Temperature | Aerobic/Anaerobic | 30° C. | Aerobic | 30° C. | Anaerobic | 30° C. | Anaerobic | 37° C. | Anaerobic | 37° C. | Anaerobic |

Test Example 1: Growth Potential in Honey Medium

Acacia honey from Romania (Yamada Bee Farm) was diluted at 10% (w/w) with purified water to prepare an aqueous honey solution having pH 8.0. This aqueous solution was sterilized at 121° C. for 5 min to produce 10% honey medium. The solid content of honey used was at least 81.6%.

The above five bacterial strains were each cultured on MRS agar medium (BD, Inc.) for 48 h under the optimal conditions to give single colonies. One of the resulting single colonies was seeded in 4 mL of MRS liquid medium (BD, Inc.) and cultured for 48 h to prepare a preparatory culture liquid. A bacterial liquid from the preparatory culture liquid was diluted with MRS liquid medium to produce a bacterial liquid at 2 McFarland turbidity (OD600=0.451) as an inoculum for main culture.

Then, 200 μL of each inoculum was seeded in 20 mL of 10% honey medium and the mixture was subjected to shaking culture at the optimal temperature. Each fermented liquid was collected at 0, 12, and 24 h after the initiation of culturing and the OD value of the fermented liquid was measured at 600 nm. The results are shown in FIG. 1.

Figure 2:
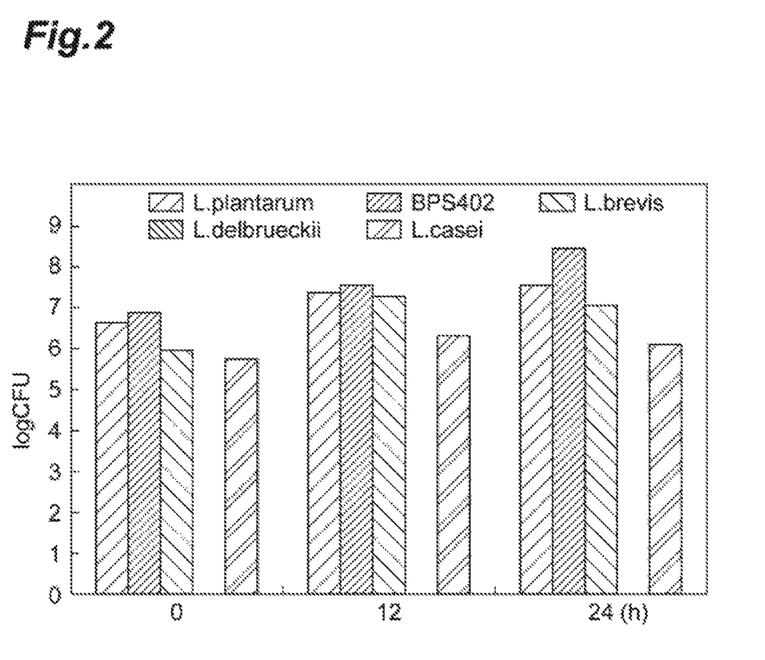
FIG. 2 is a graph showing the CFU of each bacterial strain in 10% honey medium.

Meanwhile, each fermented liquid at 0, 12, or, 24 h after the initiation of culturing was subjected to 10-fold dilution twice to 7 times. Each dilution was plated on BCP medium (BCP-added agar "Nissui" for plate counting; Nissui Pharmaceutical Co., Ltd.) by using a cell spreader. The culturing continued for 48 h under the optimal conditions and the number of colony-forming units (CFU) was then counted. The results are shown in FIG. 2.

Figure 1:
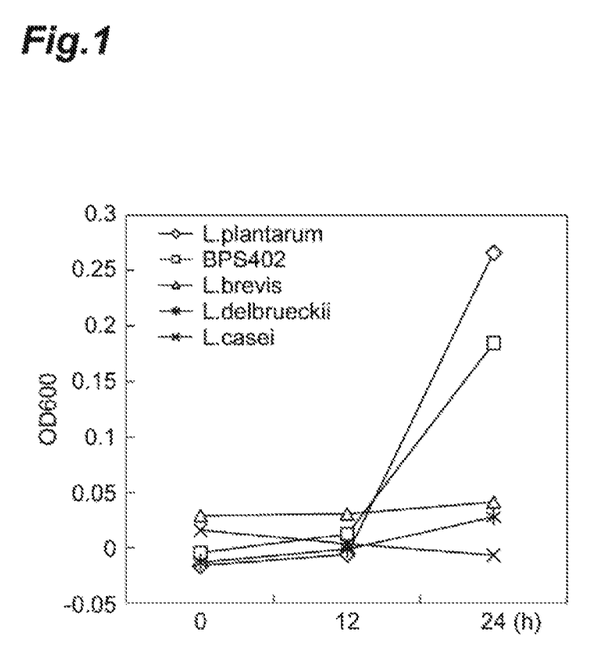
FIG. 1 is a graph showing the OD values of each bacterial strain in 10% honey medium.

As a result of culturing of the five bacterial strains in 10% honey medium, *L. plantarum* had the highest OD value, followed by BPS402 and *L. brevis* (FIG. 1). Growth of *L. delbrueckii* or *L. casei* in 10% honey medium was undetected. When the number of CFUs was counted, BPS402 had the highest colony count by 24 h after the initiation of culturing (FIG. 2). No *L. delbrueckii* colonization was found at any time points. Growth of *L. casei* was undetected but the colonization was found.

Test Example 2: Bacterial Growth Potential in Medium with Different Honey Concentrations Acacia honey from Romania was diluted at 10, 25, or 30% (w/w) with purified water to prepare an aqueous honey solution having pH 8.0. Each aqueous solution was sterilized at 121° C. for 5 min to produce 10, 25, or 30% honey medium.

BPS402, *L. plantarum* and *L. brevis* were each used to prepare an inoculum like Test Example 1. Then, 200 μL of each inoculum was seeded in 20 mL of honey medium at each concentration and was subjected to shaking culture for 48 h at the optimal temperature. Each fermented liquid was collected at 0, 12, 24, and 48 h after the initiation of culturing and the OD value and the pH at 600 nm of the fermented liquid were measured. The results are shown in FIGS. 3 and 4.

Figure 3:
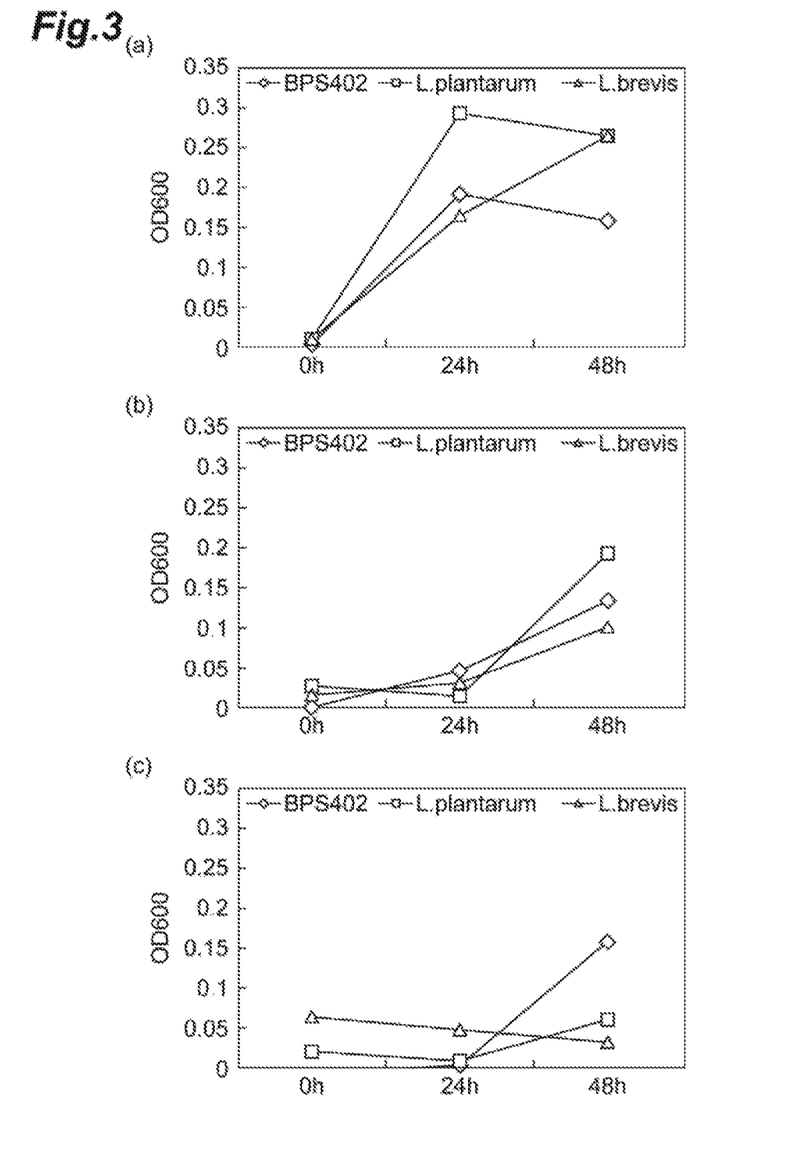
FIGS. 3(a), 3(b), and 3(c) are graphs showing the OD values of each bacterial strain in 10%, 25%, and 30% honey medium, respectively.

Any of BPS402, *L. plantarum*, and *L. brevis* was found to exhibit good growth in 10% honey medium (FIGS. 3(*a*)) and 25% honey medium (FIG. 3 (*b*)). Meanwhile, only BPS402 was found to grow in 30% honey medium (FIG. 3(*c*)).

Figure 4:
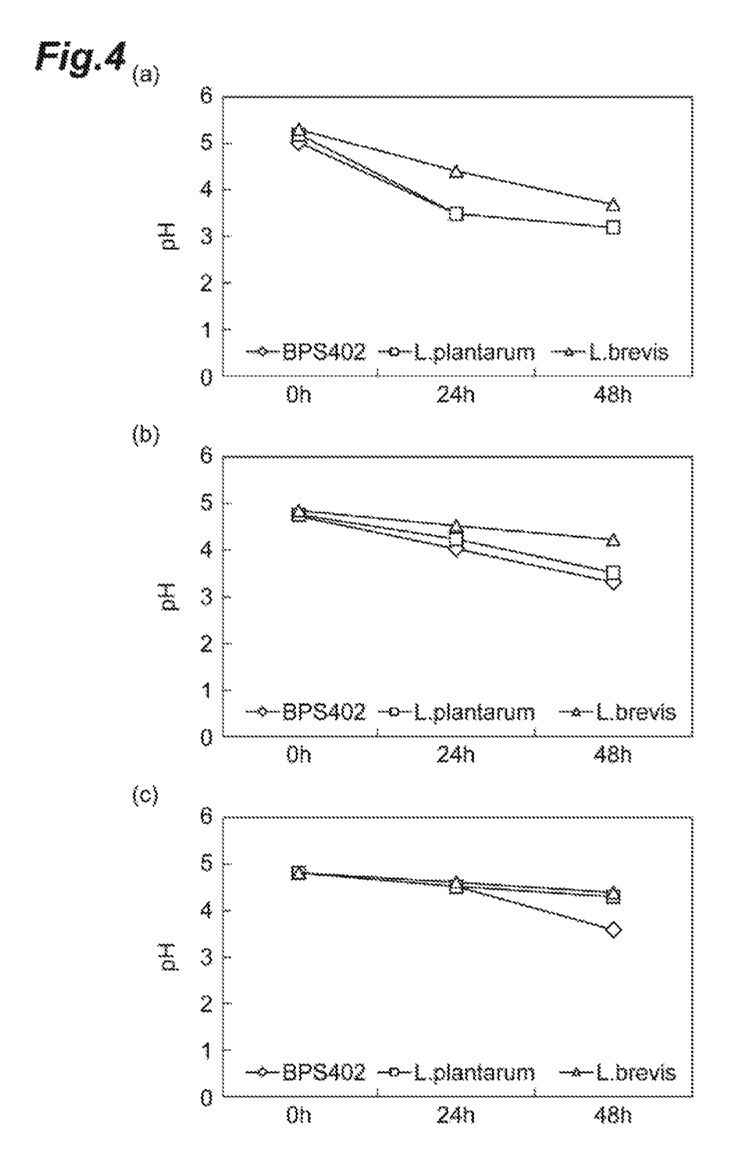
FIGS. 4(a), 4(b), and 4(c) are graphs showing the pH levels in 10%, 25%, and 30% honey medium, respectively.

Regarding any of BPS402, *L. plantarum*, and *L. brevis*, the pH of each fermented liquid obtained from the 10% honey medium (FIG. 4(*a*)) or the 25% honey medium (FIG. 4(*b*)) decreased compared to when the culturing started. By contrast, only when BPS402 was used, the pH of each fermented liquid obtained from the 30% honey medium (FIG. 4(*c*)) decreased compared to when the culturing started.

Test Example 3: HPLC Analysis of Fermented Products

Fermented liquids at 24-h and 48-h time points among the fermented liquids obtained in Test Example 2 were each filtered and sterilized through a 0.2-μm filter to prepare a sample for HPLC analysis. Prior to the HPLC analysis, each sample was again filtered through a 0.45-μm filter. Commercially available lactic acid and acetic acid were each diluted to prepare samples for a standard curve and the standard curve was then created. The retention time of lactic acid or acetic acid was 5.08 min or 5.46 min, respectively.

Figure 5:
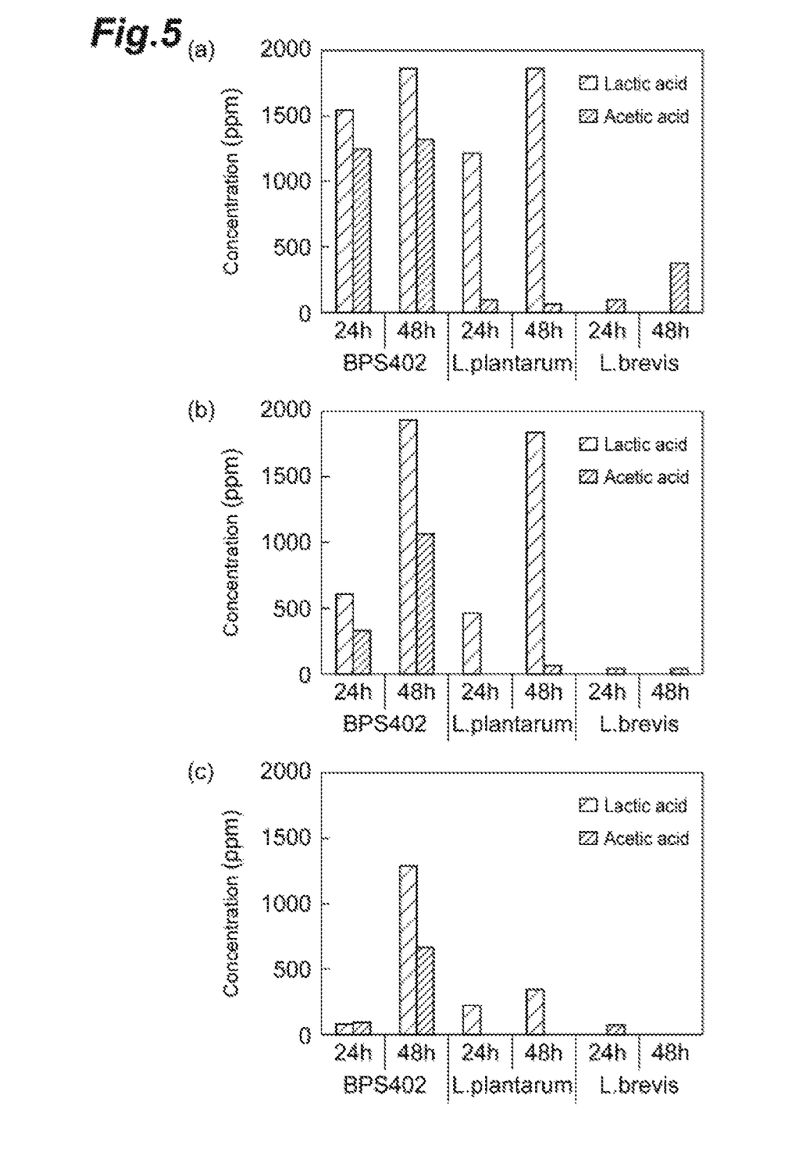
FIGS. 5(a), 5(b), and 5(c) are graphs showing the lactic acid and acetic acid concentrations in 10%, 25%, and 30% honey medium, respectively.

The lactic acid concentration and the acetic acid concentration of each fermented liquid were measured by HPLC under the following conditions. The results are shown in FIG. 5.

Column: cosmosil 5C18-AR-II 5 μm, 4.6 mm i.d.×250 mm) a-018
Mobile phase: 0.85% aqueous phosphoric acid
Flow rate: 1.0 mL/min
Column temperature: 40° C.
Detection condition: 210 nm The lactic acid concentration and the acetic acid concentration of each fermented liquid obtained by fermentation in the 10, 25, or 30% honey medium are shown in FIG. 5(a), FIG. 5(b), or FIG. 5(c), respectively, in this order. When BPS402 was used, lactic acid and acetic acid were detected in each fermented liquid obtained from the 10, 25, or 30% honey medium. When *L. plantarum* was used, lactic acid was detected in each fermented liquid obtained from the 10, or 25% honey medium. In the case of *L. brevis*, while acetic acid was somewhat detected in each fermented liquid obtained from the 10% honey medium, no lactic acid production was found in any of the fermented liquids.

The invention claimed is:

1. A fermented honey product obtained by fermenting a honey-containing material with *Lactobacillus kunkeei*, wherein the material has a honey concentration of more than 25%.

2. The fermented honey product according to claim 1, wherein the *Lactobacillus kunkeei* is *Lactobacillus kunkeei* BPS402 (accession number: FERM BP-11439).

3. A food, cosmetic, or drug, comprising the fermented honey product according to claim 1.

4. A method for producing a fermented honey product, comprising fermenting a honey-containing material having a honey concentration of more than 25% with *Lactobacillus kunkeei*.

5. The method according to claim 4, wherein the *Lactobacillus kunkeei* is *Lactobacillus kunkeei* BPS402 (accession number: FERM BP-11439).

6. A method for producing a food, cosmetic, or drug, comprising adding the fermented honey product obtained by the method according to claim 4.

7. A composition for fermentation of a honey-containing material having a honey concentration of more than 25%, the composition comprising *Lactobacillus kunkeei*.

8. The composition according to claim 7, wherein the *Lactobacillus kunkeei* is *Lactobacillus kunkeei* BPS402 (accession number: FERM BP-11439).

* * * * *